United States Patent [19]

Bowen et al.

[11] Patent Number: 4,850,707
[45] Date of Patent: Jul. 25, 1989

[54] OPTICAL PULSE PARTICLE SIZE ANALYZER

[75] Inventors: Mark S. Bowen, Medford; Michael L. Broide, Cambridge; Richard J. Cohen, Newton Highlands, all of Mass.

[73] Assignee: Massachusetts Institute of Technology, Cambridge, Mass.

[21] Appl. No.: 872,097

[22] Filed: Jun. 6, 1986

[51] Int. Cl.[4] ...................... G01N 15/02; G01N 21/53
[52] U.S. Cl. ...................................... 356/336; 356/338
[58] Field of Search ................................. 356/336, 338

[56] References Cited

U.S. PATENT DOCUMENTS

| 3,873,204 | 3/1975 | Friedman et al. | 356/39 |
| 4,072,421 | 2/1978 | Coyne et al. | 356/338 |
| 4,080,264 | 3/1978 | Cohen et al. | |
| 4,174,952 | 11/1979 | Cannell et al. | |
| 4,178,103 | 12/1979 | Wallace | 356/338 |
| 4,606,631 | 8/1986 | Anno et al. | 356/338 X |

OTHER PUBLICATIONS

Applied Optics/vol. 12, No. 3/3/1973, "Low Angle Laser Light Scattering–Absolute Calibration", pp. 541–550, Kaye et al.
Analytical Chemistry/vol. 45, No. 2/2/1973, "Low-Angle Laser Light Scattering", pp. 221 A–225A, Kaye.
von Schulthess, G. K. et al., Macromolecules 13:939 (1980).
von Schulthess, G. K. et al., Macromolecules 16:434 (1983).
Cohen, R. J. and Benedek, G. B., Immunochemistry 12:349 (1975).
von Schulthess, G. K. et al., Immunochemistry 13:955 (1976).
von Schulthess, G. K. et al., Immunochemistry 13:963 (1976).
von Schulthess, G. K. et al., Molecular Immunology 17:81 (1980).
"Experimental Analysis of Diffusion Controlled Coagulation Using an Optical Pulse Particle Size Analyzer", Bowen, M. S. et al., Kinetics of Aggregation and Gelation, (1984).
Bowen et al., J. of Colloid and Interface Science, vol. 105, No. 2, p. 605, Jun. 1985.
Bowen et al., J. of Colloid and Interface Science, vol. 105, No. 2, pp. 617–627, Jun. 1985.

Primary Examiner—David C. Nelms
Assistant Examiner—Matthew W. Koren
Attorney, Agent, or Firm—Hamilton, Brook, Smith & Reynolds

[57] ABSTRACT

A system for determining the cluster size distribution of submicron-size particles in a solution by optical pulse particle size analysis is provided. The system comprises a laminar flow cell having a translucent chamber, means for passing a sheath liquid and a sample liquid through the chamber, a light source and means for focusing the beam of light onto the chamber of the flow cell, a collecting lens, means for limiting collected light to a low angle, a stop, an iris, a light sensor and a means for processing the light signals. The system employs a combination of improved features which allows ultra-sensitive measurement of the cluster size distribution of particles, and can reliably detect as few as three dimers for every 10,000 monomers of micron size particles.

6 Claims, 5 Drawing Sheets

OPTICAL PULSE PARTICLE SIZE ANALYZER

The government has rights in this invention pursuant to Grant Number PCM-8013689 awarded by the National Science Foundation.

BACKGROUND OF THE INVENTION

The determination of size distributions in dispersions of submicrometer particles represents an important problem in physics, chemistry, biology, and engineering. The size distribution determines many bulk properties of a dispersion and provides detailed information about the mechanisms governing both the kinetics and thermodynamics of aggregation.

A number of techniques have been developed to characterize such size distributions. The most prevalent is light scattering, which has mainly been used to measure bulk properties of colloidal dispersions and aerosols. Various weighted averages of the particle size distribution may be deduced from the turbidity of the solution, or its temporal correlation function. With more polydisperse samples, it becomes increasingly difficult to characterize the distribution using these techniques. Consequently, single particle techniques which measure the distribution itself have emerged.

Resistive pulse analysis, invented by Coulter in 1949, is the most widely used single-particle sizing method. See U.S. Pat. No. 2,656,508. While commercial Coulter counters are designed for particles larger than 1 micron, a nanopar resistive pulse analyzer developed by Deblois and Bean in 1970 has been used to detect the aggregation of 235-nm latex spheres. Since the resistive pulse technique requires electrolytic solvents, it is of limited utility when salt is an experimental parameter. Alternatively, some single-particle counters measure fluorescence or scattered light intensity. Flow cytometry has combined all three detection techniques with digital signal processing and hydrodynamic focusing in an extensive effort to characterize and sort individual mammalian cell particles larger than 1 micron.

Another technique for measuring cluster size distribution of particles designated optical pulse particle size analysis is described by Bowen et al. in *Kinetics of Aggregation and Gelation,* F. Family, D. P. Laudau eds. Elsevier Science Publishers, 1984. Optical pulse, particle size analysis is based on a discovered relationship between low angle scattered light intensity and cluster size of uniform size particles. For such particles, the intensity of light scattered, in the low angle limit, is proportional to the square of the number of particles in a cluster. This "$n^2$ dependence" (where n is the number of particles in a cluster) holds for particles up to about three times the wavelength of incident light.

The authors also describe a optical pulse particle size analyzer for measuring cluster size distribution. Clusters are passed, single file, through an optical flow cell, which is uniformly illuminated by a focused laser beam. As the clusters pass through the illuminated volume they scatter light. This scattered light is collected at low angles (3°) and imaged on the surface of a photomultiplier tube. The generated photocurrent pulses are then passed through an analog square root amplifier and finally sorted on a multichannel pulse-height analyzer. The resulting histogram consists of a series of linearly spaced peaks—each corresponding to a different size n-mer.

DISCLOSURE OF THE INVENTION

The invention pertains to an improved system for determination of cluster size distribution by optical pulse particle size analysis. The system employs a combination of improved features which provides ultra-sensitive measurement of cluster size distribution of particles. The instrument can reliably detect as few as 3 dimers for every 10,000 monomers of micron size particles.

The system, in general, comprises:

a. a laminar flow cell for passage of a sheath liquid and a sample liquid containing suspended, clustered particles whose cluster size distribution is to be determined, the flow cell having a translucent chamber configured to constrain the suspended particles to passage in single file through the chamber;

b. means for passing the sheath liquid through the chamber at a continuous flow rate;

c. means for passing the sample liquid through the chamber, in stream with the sheath liquid, at a continuous rate of flow;

d. a light source for generating a beam of light;

e. focusing means for focusing the beam of light onto the translucent chamber of the flow cell such that the beam is substantially perpendicular to the direction of particle flow through the chamber;

f. a lens for collecting pulses of light scattered from the particles in the sample liquid;

g. means for limiting the collected light to light scattered from the particles up to 5.2 degrees from the axis of the beam of light;

h. light sensing means for sensing the intensity of scattered light collected by the lens and for converting the sensed light pulse to an electrical signal proportional to the intensity of the scattered light pulse; and i. signal processing means for determining the cluster size distribution of particles.

In a preferred embodiment, the pump means for passing the sample liquid into the sheath liquid stream and through the chamber is an infusion pump, for example, a screw-feed infusion pump. The light source is a laser. The focusing means are such that the light beam is constricted to an elliptical shape so that the direction of particle flow is along the minor axis of the ellipse. In this way, the sensing zone is minimized. Cylindrical lenses can be used for this purpose. Additionally, the means for limiting the collected scattered light to angle up to about 5.2 degrees from the axis of the beam of light comprises:

(i) a stop, preferably a metal strip, located between the lens and the flow cell in the path of the beam of light transmitted through the flow cell, for diverting the transmitted beam of light from its axis; and (ii) an iris, located between the stop and the lens, the iris having a diaphragm of a diameter which excludes light scattered at angles of greater than about 5.2 degrees from the axis of the beam of light.

A collecting lens is employed which provides a magnified pulse image to the sensing means. The sensing means is a photomultiplier tube and the signal processing means includes means for assessing the maximum of the electrical signal.

BEST MODE FOR CARRYING OUT THE INVENTION

Figure 1:
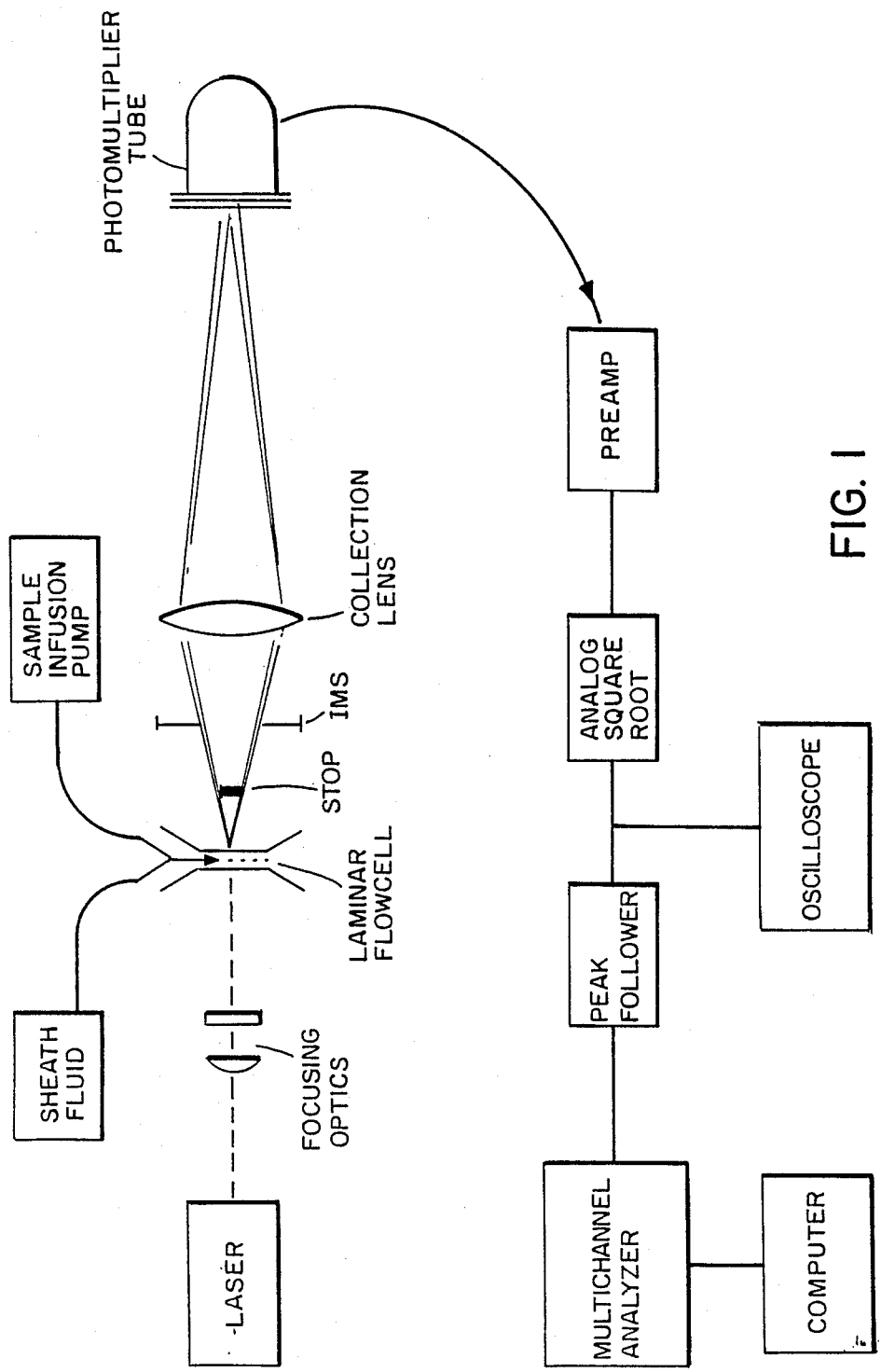
FIG. 1 is a block diagram of the optical pulse particle size analyzer of this invention.

FIG. 1 shows the overall system of the invention in block diagram form. In order to obtain a single file stream of particles a laminar flow cell (Ortho Diagnostics, Part No. 300-0511-000) is used. This cell has an inside square passageway 250 microns on edge through which sheath fluid is run. The sheath fluid is chosen to be the same as the sample solvent containing suspended particles. This avoids any optical discontinuity that would occur if sheath fluid and sample liquid were different. Furthermore, unequal osmotic strengths of sheath and sample streams would destroy the laminar flow and degrade the signal quality. Once selected, the sheath fluid is prefiltered (Gelman Mini capsule, 0.2 micron), and then in-line filtered (Millipore Millex-GS, 0.22 micron) from the nitrogen pressurized sheath bottle. To accurately detect submicron particles it is important that the sheath be substantially totally particle free. To insure that no bacteria colonizes sodium azide or other bacteriocide can be added to sheath liquid stock.

The sample containing particles to be analyzed is injected into the sheath liquid flow using a continuous infusion pump (e.g. Harvard Apparatus, model 944). A continuous screwfeed pump provides very reproducible volume injections, within 1% for integer revolutions of the pump's screw-feed. Such accuracy is not possible with a pressure feed injection, as used in most commercial flow cytometers. To maintain this 1% precision requires that the dead volume must be purged in the feed lines with approximately 0.5 cc of sample before taking a measurement. It is only with this painstaking care that actual concentrations, number of particles per cc, instead of just the relative abundance of one-sized particles to another can be ascertained.

Typical flow rates for the flow cell are: sheath 50 cc/hr. sample 3.3 cc/hr. This results in a sample stream of approximately 10 microns in diameter. However, by varying the sample injection rate, larger or smaller sample streams can be obtained.

Having constrained the particles to a single file passage through the flow cell an argon-ion laser beam (SpectraPhysics Model 164-06) is directed at right angles to the flow so that as each particle crosses the beam it scatters a pulse of light. The beam is focused using two cylindrical lenses (f=100 mm, f=40 mm) to produce an elliptical spot at the flow cell approximately 200×30 microns, with its major axis perpendicular to the particle stream. In this case since the sample stream is never wider than 20 microns, this ensures uniform illumination of the particles; thus differences in scattered intensity are due to differences in particle sizes, not to their location in the beam. The elliptical minor axis of the beam is chosen small, to minimize illumination of the flow cell and sample stream parallel to the flow and thereby reduce the total background light.

Scattered light from the particles at very low angles (up to 5.2° is collected, generally between 1.7 and 3.5). At these low angles the scattered intensity from clusters of spheres is proportional to $n^2$—where n is the number of units in a cluster —and is independent of the cluster's orientation within the beam, or the cluster's particular configuration. Although this results is expected to hold for clusters small compared to the wavelength of light, the surprising result is that it holds for clusters comparable to the wavelength as well. The larger collection angle is determined by the numerical aperture of the microscope objective (f=40 mm) which is placed on axis with the laser beam. The smaller angle is set by the size of the stop preferably a metal strip—placed in front of the collection lens—which is used to stop the transmitted laser beam. The image from this lens is then further magnified by another lens (f=50 mm) to form a compound magnification of ×80 at the iris and slit preceeding the photomuliplier tube (EMI Model 9789b). The slit is oriented perpendicular to the sample flow and is narrowed to minimize the scattering volume, as is the iris. Reducing the stray light to the phototube is an essential step in obtaining a good signal-to-noise ratio.

Optical components can be mounted on micro adjustable translation platforms as to allow for precise alignment. The entire instrument can be built upon an optical table with vibration isolating less (Newport Research Corporation).

As each particle crosses the laser beam, its scattered pulse of light is detected by the phototube and converted into a pulse of electrical current. With particles moving at 100 cm/sec, they cross the scattering volume in about 20 microseconds. In order to properly process these fast pulses a special purpose pre-amp and peak-follower is used.

The first stage of this pre-amp is a current-to-voltage converter. This is followed by a lowpass filter (10 MHz, 2-pole) to remove any high frequency noise. Finally, there is a dc offset adjustment to zero-out any dc light levels. An offset instead of a high-pass filter is used to avoid the settling problems encountered with ac-coupling a pulsed signal. Off-scale pulses are processed so that all the particles in the sample are counted—even if they cannot be sized. All of these functions are done using Analog Devices AD380 operational amplifiers, selected for their large band-width and fast-settling time (300 MHz). An oscilloscope provides us with continuous monitoring of the signal.

In addition to the pre-amp, an optional square root device (AD429) is employed to compress the output range of our signal. Since for clusters of spheres we anticipate an $n^2$ dependence, a square root device gives us a linear response in n, which simplifies interpretation of the histograms.

If the signals were perfectly smooth pulses, the signals could be sent directly into the A/D convertor on the multichannel analyzer (Norland Corp. model IT-5400). However, since the A/D only searches for local maximum of a pulse, an analog peak-follower which first searches for the global maximum of the pulse, and then sends that voltage to the A/D is employed. The result of the signal processing is a pulse-height distribution directly related to the particle-size distribution. Histograms are transferred to a minicomputer for subsequent analysis.

As with the sheath fluid, the solvent of the dispersion must be optically clear. This level of purity is obtained by making up all solvents with Milli-Q water (Millipore reagent grade water system) which has been terminally filtered with a 0.22 micron filter. Aliquots are drawn using Becton Dickinson (BD) plastic syringes and further filtered with Millex-GS 0.22 micron filters to insure a clean transfer. The vessels used for mixing the sample are carefully cleaned by first washing with Micro Cleaning Solution (International Products Corp, N.J.), then rinsing with Milli-Q water, and finally rinsing with the solvent to be used. We find that only Parafilm (American Can Co., CT) provides us with a particle-free closure. Other covers, especially ground glass, tend to shed into the sample.

As a last check to verify that the solvent is clean, before adding the particles, we place the (square-sided) vessel in a laser beam and look for low-angle scattering from dust or debris. The signature of a clear solvent is the faint glow from the beam and the absence of bright flashes.

Figure 2:
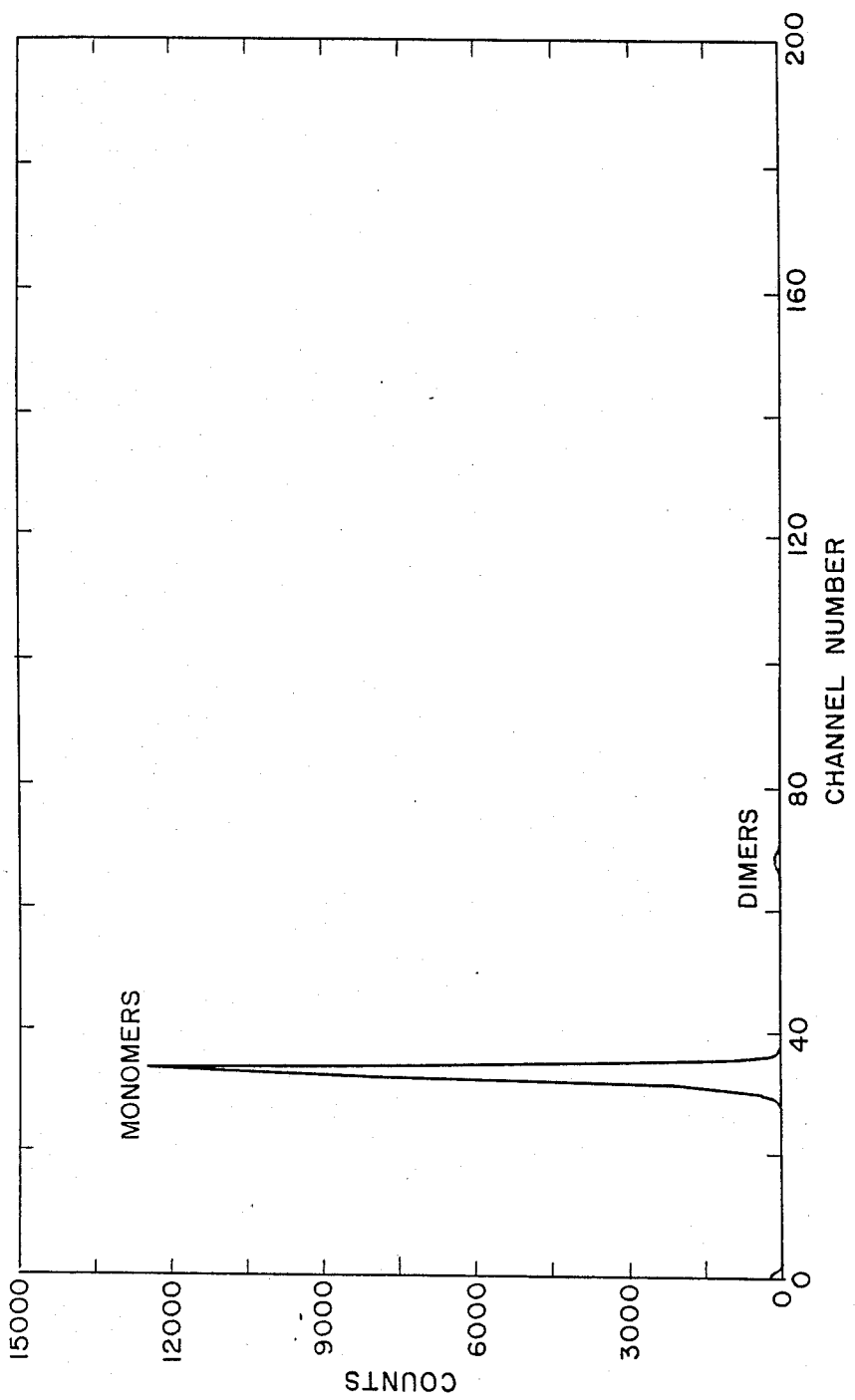
FIGS. 2-5 are histograms of the cluster size distribution of 0.5 micron particles as determined by the system of this invention.
Figure 3:
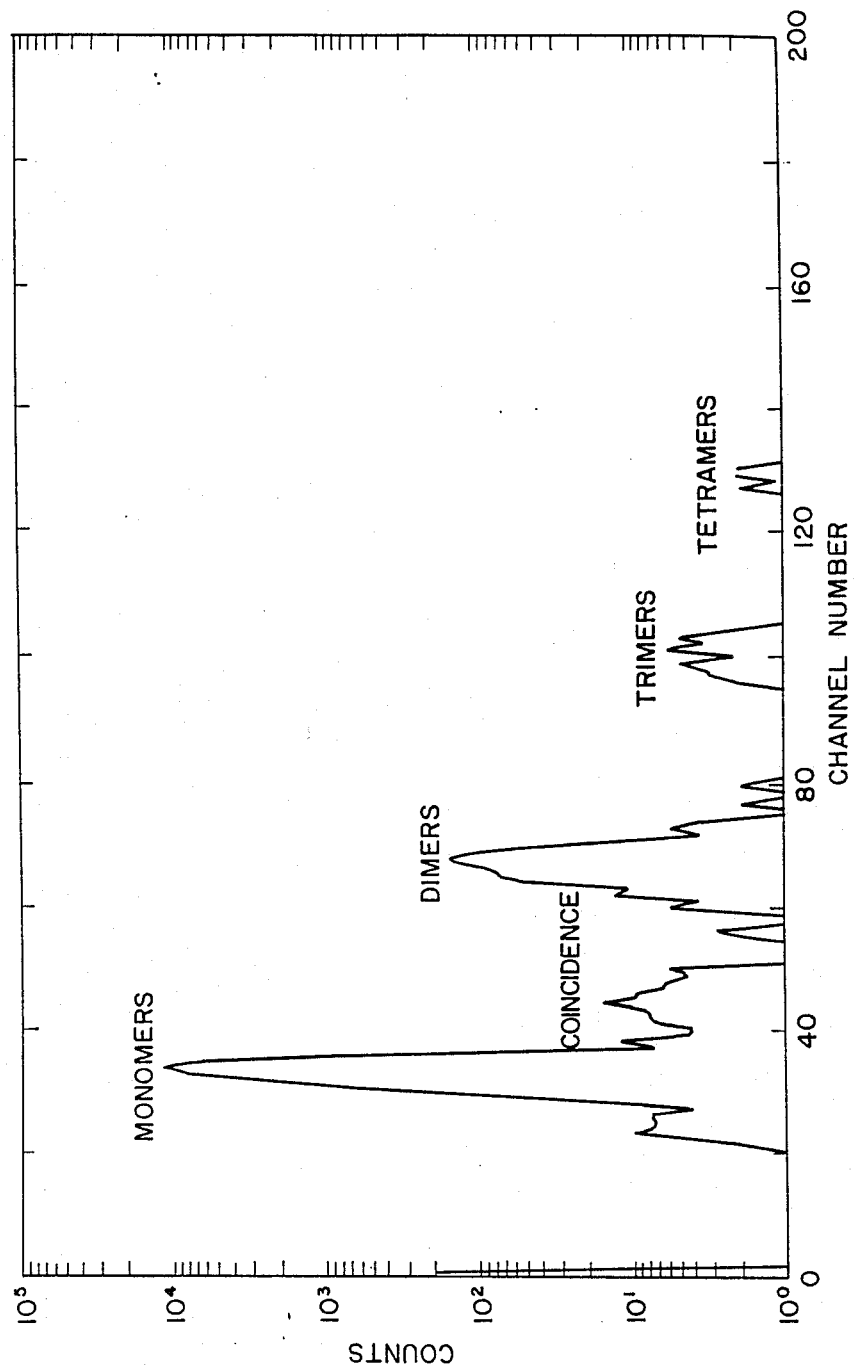

Although the instrument detects particles 0.1 microns in diameter, all the histograms used to illustrate the instrument's performance were 0.5 micron making sample preparation and instrument alignment less tedious. FIG. 2 is a histogram of a monomeric sample. The first peak represents the monomers, the second, smaller one, the dimers. The width of the monomer peak is solely due to the variation in monomer size, as reported by the sphere's manufacturer, and indicated a well aligned instrument. Plotting this same histogram with a log scale for the number of counts reveals more structure, FIG. 3. The peak between the monomers and dimers is a coincidence peak representing two unbound monomers in the scattering region and indicated the need for a more dilute sample to avoid this. Also evident on the log scale are the peaks corresponding to the trimers and tetramers. The number of tetramers to monomers is 3.2:10,000, a sensitivity only possible through meticulous cleanliness of sample and sheath.

Figure 4:
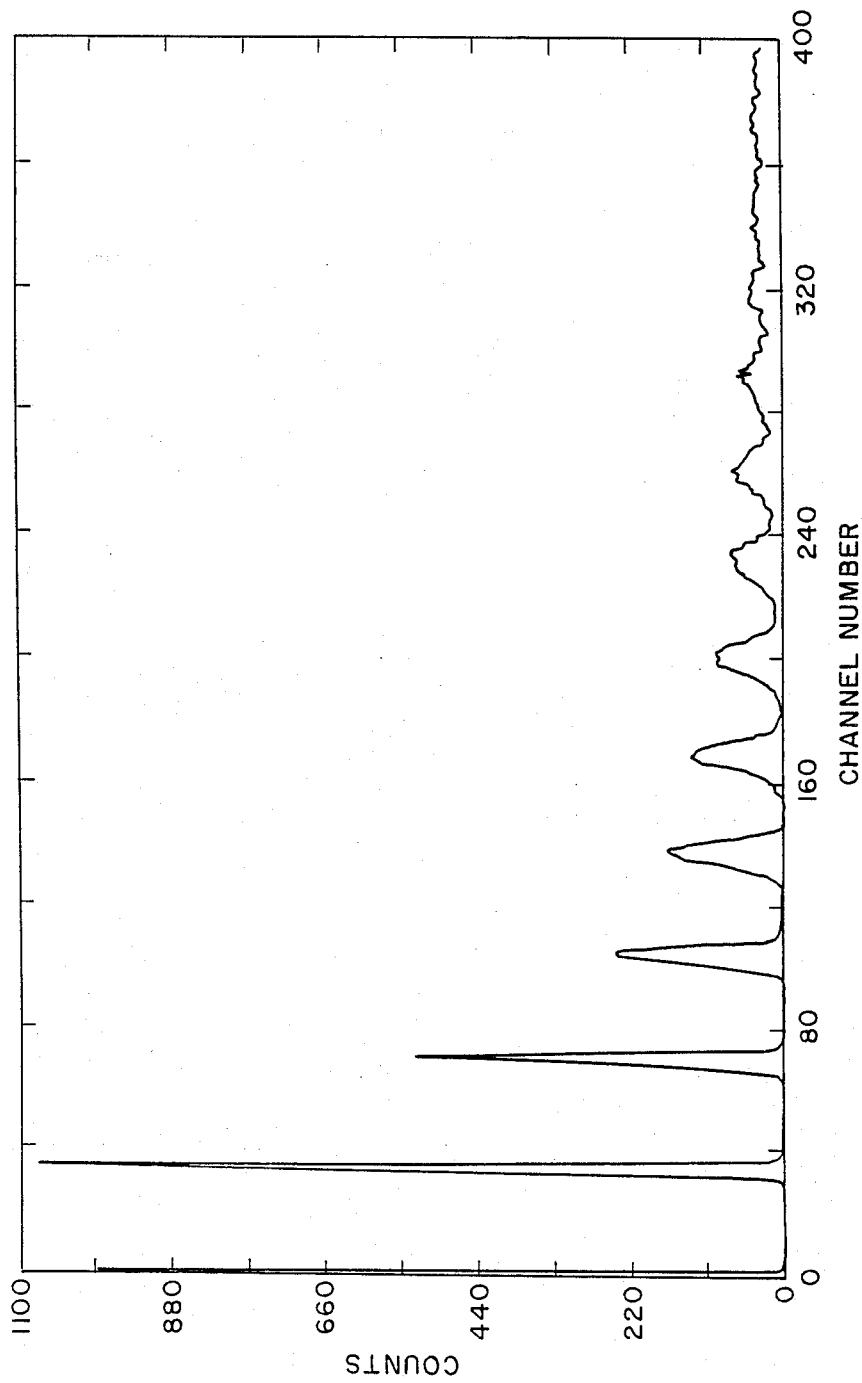

In a more highly aggregated sample of spheres, FIG. 4, shows eleven linearly spaced peaks. This resolution is by far the best ever obtained from a single particle instrument. It is believed attributable to the refined optical and electronic designs and employment of a laminar flow cell. For smaller monomers even better resolution is achieved up to fourteen peaks for 0.31 micron spheres, in accord with our light scattering analysis.

Figure 5:
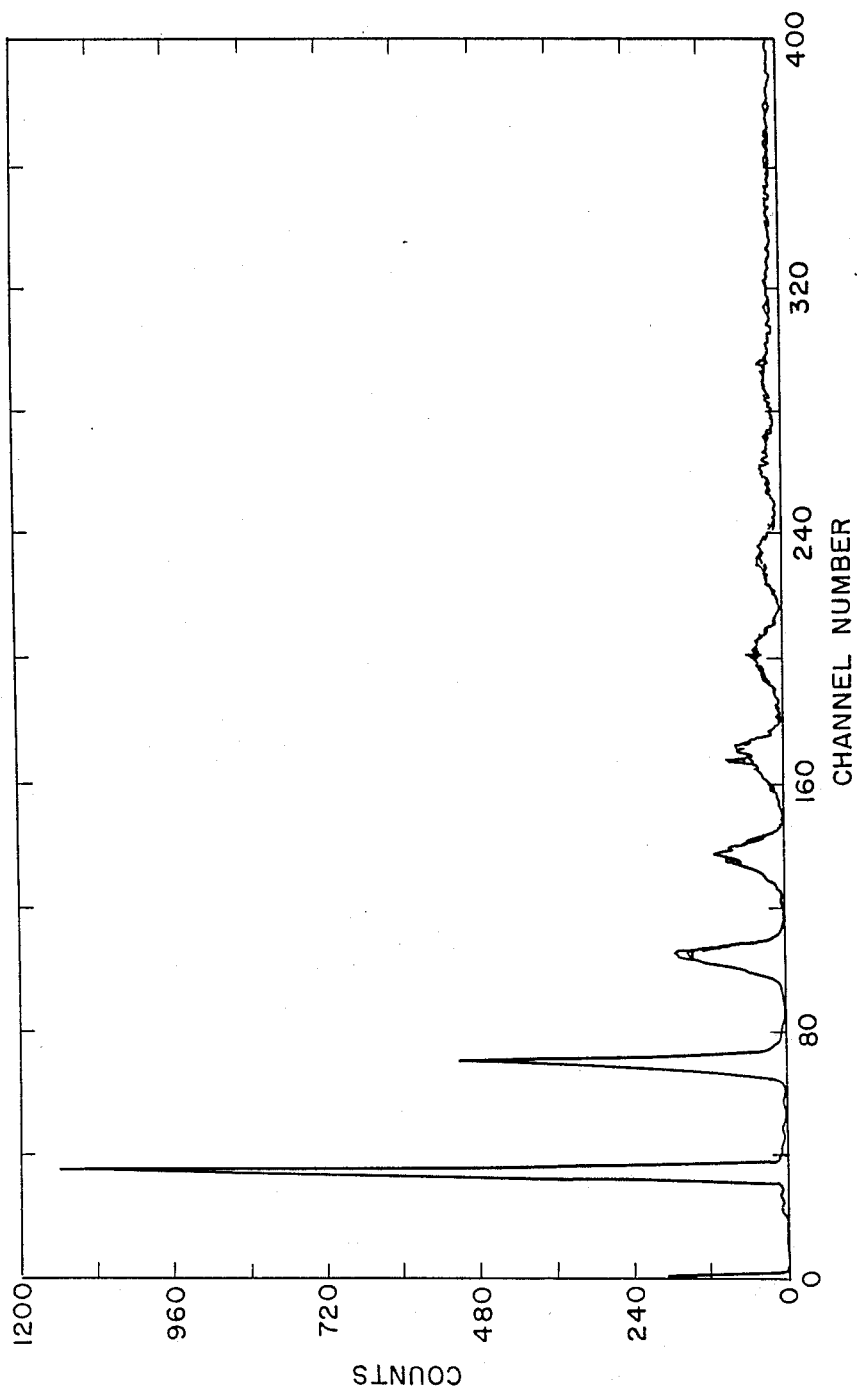

As a final test of the instrument we collected, under identical conditions, three sequential histograms, FIG. 5. The fact that these curves are nearly superimposable illustrated the excellent reproducibility of our instrument. Such consistency ducibly infuse the sample; and using proper electronics which correctly record every event. In addition, once aligned our optical train proves to be very stable, needing little or no adjustment, further adding to the confidence in our measurement.

Industrial Applicability

The optical pulse particle size analyzer of this invention can be used to characterize industrial suspensions such as paint or clay. In the medical field, the system can be used to size distribution of agglutinated particles. This provides for extremely sensitive immunoassay for antigens and antibodies based upon agglutination reactions.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A system for determining the cluster size distribution of submicron-size particles suspended in a liquid, comprising:
   a. a laminar flow cell for passage of a sheath liquid and a sample liquid containing suspended, clustered particles, the flow cell having a translucent chamber configured to constrain the suspended particles to passage in single file through the chamber;
   b. means for passing the sheath liquid through the chamber at a continuous flow rate;
   c. infusion pump means for passing the sample liquid into the sheath liquid stream and through the chamber at a continuous rate of flow;
   d. a light source for generating a beam of light;
   e. focusing means for focusing the beam of light onto the translucent chamber of the flow cell such that the beam is substantially perpendicular to the direction of particle flow through the chamber, wherein the focusing means comprises one or more cylindrical lenses which constricts the light beam to an elliptical shape such that the direction of flow of the particles through the chamber is along the minor axis of the ellipse;
   f. a collecting lens for collecting pulses of light scattered from the particles in the sample liquid;
   g. means for limiting the collected light to light scattered from the particles up to 5.2 degrees from the axis of the beam of light;
   h. a stop, located between the lens and the flow cell in the path of the beam of light transmitted through the flow cell, which stop diverts the transmitted beam of light from its axis;
   i. an iris, located between the stop and the lens, having a diaphragm of a diameter which excludes light scattered at angles greater than about 3.0–5.2 degrees from the axis of the beam of light;
   j. light sensing means for sensing the intensity of scattered light collected by the lens and for converting the sensed light pulse to an electrical signal proportional to the intensity of the scattered light pulse; and
   k. signal processing means for determining the cluster size distribution of particles.

2. A system of claim 1, wherein the light source is a laser.

3. A system of claim 1, wherein the light sensing means for sensing the intensity of pulses of scattered light comprises a photomultiplier tube.

4. A system of claim 1, wherein the signal processing means includes means for assessing the maximum of the electrical signal.

5. A system of claim 4, wherein the means for assessing the maximum of the electrical signal further comprises a pre-amplifier system and a peak-follower for processing fast pulses of light scattered by particles crossing the laser beam.

6. A system of claim 5, wherein the pre-amplifier system further comprises a current-to-voltage converter followed by a lowpass filter for removing low frequency noise, a dc offset adjustment for zeroing out any dc light levels, and a square-root device for compressing the output range of the signal.

* * * * *

UNITED STATES PATENT AND TRADEMARK OFFICE
CERTIFICATE OF CORRECTION

PATENT NO.   :  4,850,707
DATED        :  July 25, 1989
INVENTOR(S)  :  Michael L. Broide, et al.

It is certified that error appears in the above-identified patent and that said Letters Patent is hereby corrected as shown below:

On the title page:

Item [19] Bowen et al., should read --Broide, et al.--

The order of the inventors names should be:

1. Michael L. Broide
2. Mark S. Bowen
3. Richard J. Cohen

Signed and Sealed this

Twenty-second Day of May, 1990

*Attest:*

HARRY F. MANBECK, JR.

*Attesting Officer*         *Commissioner of Patents and Trademarks*